US011660079B2

(12) United States Patent
Wiygul (10) Patent No.: US 11,660,079 B2
(45) Date of Patent: May 30, 2023

(54) CATHETER SYSTEM AND METHOD OF USE (71) Applicant: Cornell University, Ithaca, NY (US)

(72) Inventor: Jeremy B. Wiygul, Little Neck, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 426 days.

(21) Appl. No.: 16/641,550

(22) PCT Filed: Aug. 29, 2018

(86) PCT No.: PCT/US2018/048634
§ 371 (c)(1),
(2) Date: Feb. 24, 2020

(87) PCT Pub. No.: WO2019/046486
PCT Pub. Date: Mar. 7, 2019

(65) Prior Publication Data
US 2020/0187918 A1 Jun. 18, 2020

Related U.S. Application Data (60) Provisional application No. 62/552,767, filed on Aug. 31, 2017.

(51) Int. Cl.
*A61B 10/00* (2006.01)
*A61M 25/00* (2006.01)
*A61M 39/24* (2006.01)

(52) U.S. Cl.
CPC ....... *A61B 10/007* (2013.01); *A61M 25/0045* (2013.01); *A61M 25/0068* (2013.01);
(Continued)

(58) Field of Classification Search
CPC ............ A61B 10/007; A61M 25/0045; A61M 25/0068; A61M 39/24; A61M 2025/0004;
(Continued)

(56) References Cited

U.S. PATENT DOCUMENTS 3,774,591 A * 11/1973 Corbin ................. A61B 10/007
600/580
4,756,708 A * 7/1988 Martin ................... A61B 10/04
600/581
(Continued)

FOREIGN PATENT DOCUMENTS

CN 206167607 U 5/2017
FR 2855399 A1 12/2004
(Continued)

OTHER PUBLICATIONS

International Search Report and Written Opinion dated Dec. 7, 2018 in PCT Application No. PCT/US2018/048634.

*Primary Examiner* — Susan S Su
*Assistant Examiner* — Eric Rassavong
(74) *Attorney, Agent, or Firm* — McDermott Will & Emery LLP (57) ABSTRACT

Urinary tract infections UTI may be over-diagnosed in very young children because of contamination of a urine specimen by external bacteria when using a conventional catheter. The subject matter disclosed herein relates to a coaxial catheter system and methods for its use, comprising an outer catheter that shields the distal collection opening of an inner catheter during insertion of the system through the meatus. Once the system has been deployed, the distal opening of the inner catheter is exposed in order to collect uncontaminated urine. The system may include a variety of mechanisms to advance the inner catheter relative to the outer, or to retract the outer catheter relative to the inner, a halting mechanism to limit distal movement of the outer catheter, a stopping mechanism to limit distal movement of the inner catheter, and a stabilization mechanism to hold the deployed system in place in male patients.

24 Claims, 7 Drawing Sheets (52) U.S. Cl.
CPC ..... *A61M 39/24* (2013.01); *A61M 2025/0004* (2013.01); *A61M 2025/0047* (2013.01); *A61M 2025/0056* (2013.01); *A61M 2039/2426* (2013.01); *A61M 2210/1089* (2013.01)

(58) Field of Classification Search
CPC .. A61M 2025/0047; A61M 2025/0056; A61M 2039/2426; A61M 2210/1089; A61M 2025/0175; A61M 25/0017; A61M 25/007
See application file for complete search history.

(56) References Cited

U.S. PATENT DOCUMENTS

| | | | | |
|---|---|---|---|---|
| 5,505,710 | A * | 4/1996 | Dorsey, III | A61M 1/84 604/164.11 |
| 5,665,308 | A * | 9/1997 | Watanabe | G01N 33/493 422/419 |
| 6,716,182 | B2 * | 4/2004 | Inoue | A61B 10/0045 600/581 |
| 8,323,279 | B2 * | 12/2012 | Dahla | A61B 18/1402 606/41 |
| 8,475,482 | B2 * | 7/2013 | Palmer | A61M 1/0023 606/170 |
| 8,496,632 | B2 * | 7/2013 | Shelton, IV | A61B 17/3439 604/264 |
| 8,574,218 | B2 * | 11/2013 | O'Day | A61M 25/0021 604/27 |
| 8,932,270 | B2 * | 1/2015 | O'Day | A61M 25/00 604/523 |
| 9,326,784 | B2 * | 5/2016 | Ravikumar | A61B 17/221 |
| 9,962,519 | B2 * | 5/2018 | Charest | A61M 25/0029 |
| 2003/0208220 | A1 * | 11/2003 | Worley | A61N 1/056 606/190 |
| 2006/0229573 | A1 | 10/2006 | Lamborne | |
| 2009/0171241 | A1 * | 7/2009 | Garcia | A61B 10/007 600/563 |
| 2012/0316415 | A1 * | 12/2012 | Gilbert | A61B 5/6852 600/367 |
| 2012/0323175 | A1 * | 12/2012 | Vogelbaum | A61M 25/0102 604/95.04 |
| 2013/0245496 | A1 * | 9/2013 | Wells | A61M 25/0017 600/581 |
| 2013/0274600 | A1 | 10/2013 | Jenkins et al. | |
| 2015/0112228 | A1 * | 4/2015 | Ekema | A61F 5/4408 604/385.03 |
| 2015/0257695 | A1 * | 9/2015 | Addington | G16H 50/20 600/301 |
| 2015/0320971 | A1 * | 11/2015 | Leeflang | A61L 29/14 427/2.3 |
| 2016/0001037 | A1 * | 1/2016 | Hong | A61M 27/00 206/364 |
| 2016/0199616 | A1 * | 7/2016 | Dye | A61M 25/0017 604/544 |
| 2016/0331935 | A1 * | 11/2016 | Saatchi | A61M 25/0606 |
| 2017/0000990 | A1 | 1/2017 | Gerrans et al. | |
| 2017/0080186 | A1 * | 3/2017 | Salahieh | A61M 25/0147 |
| 2017/0095646 | A1 * | 4/2017 | Norman | A61M 25/0147 |
| 2017/0266031 | A1 * | 9/2017 | Sanchez | A61F 5/4404 |

FOREIGN PATENT DOCUMENTS

| | | |
|---|---|---|
| WO | 2007067961 A2 | 6/2007 |
| WO | 2011011023 A1 | 1/2011 |
| WO | 2012079581 A1 | 6/2012 |
| WO | 2015013251 A1 | 1/2015 |

* cited by examiner

CATHETER SYSTEM AND METHOD OF USE

RELATED APPLICATIONS

The present application is a United States National Phase under 35 U.S.C. § 371 of International Application No. PCT/US2018/048634, entitled "CATHETER SYSTEM AND METHOD OF USE" and filed on Aug. 29, 2018, which claims priority to, and the benefit of, U.S. Provisional Patent Application No. 62/552,767, titled "CATHETER SYSTEM AND METHOD OF USE" and filed on Aug. 31, 2017, the entire contents of both of which are hereby incorporated by reference for all purposes.

FIELD OF THE INVENTION

The present subject matter relates generally to the field of medical devices and more specifically to catheters for the collection or drainage of a biological sample.

BACKGROUND OF THE INVENTION

A urinary tract infection UTI is an infection in any part of the urinary system including the kidneys, ureters, bladder and urethra. Most UTIs involve the lower urinary tract, meaning the bladder and the urethra. Infection limited to the bladder can be uncomfortable and even painful. However, it can become a medical emergency with serious consequences if the UTI spreads to the kidneys. Symptoms of a lower UTI include pain with urination, frequent urination, and feeling the need to urinate despite having an empty bladder. Symptoms of a kidney infection include fever and lower back pain usually in addition to the symptoms of a lower UTI.

The most common cause of an UTI is the presence of the bacteria *Escherichia coli* (*E. coli*), though other bacteria and fungi may also contribute to an infection. Clinical diagnosis involves assessment of symptoms as well as a bacterial culture of the patient's urine sample to determine the presence of bacteria in the urine and thus possibly in the bladder. UTIs are commonly treated with a short course of antibiotics. However, for more advanced or complicated cases, hospitalization might be required.

UTIs are one of the most common diagnoses in children, and in those under two years of age it has been associated with urinary tract damage. Due to the anatomy of patients under two years of age, specifically girls and uncircumcised boys, when UTI is to be determined using a bacterial culture, it is difficult to obtain a urine specimen that is not contaminated with perimeatal bacteria. The perimeatal bacteria are the bacteria naturally found around the external opening of the urethra. This contamination may lead to a number of false positive results and potentially lead to unnecessary, improper or ineffective medical interventions.

SUMMARY OF THE INVENTION

The subject matter disclosed herein relates to a catheter system for sterile collection of a biological sample from a patient. The catheter system includes an inner catheter having one or more openings along the lateral aspect of its distal end and an opening at or about its proximal end, an outer catheter coaxial with the inner catheter, a proximal handle that mechanically engages both catheters and allows the two catheters to move together while the distal opening of the inner catheter is covered by the outer catheter, and a linear actuator that enables the catheters to move independently of each other over a fixed distance to cause exposure of the distal opening or openings of the inner catheter. The linear actuator is also configured to limit the relative linear motion to be within a predefined range.

The linear actuator can be implemented in a variety of ways. In one implementation, a threaded nut is rotatably mounted to the handle. In an implementation, the threaded nut is configured such that when rotated, the nut causes linear motion of the inner catheter in a distal direction relative to the outer catheter. In another implementation, the nut causes linear motion of the outer catheter in a proximal direction relative to the inner catheter. In another implementation, the linear actuator is a manual slide mechanism is coupled to the outer catheter or handle, and can be moved in a proximal direction to cause retraction of the outer catheter relative to the inner catheter. In another implementation, the linear actuator is a manual slide mechanism coupled to the inner catheter or handle, and can be moved in a distal direction to cause advancement of the inner catheter beyond the distal end of the outer catheter. In some implementations, the linear actuator limits the amount of movement of one catheter relative to the other to between 1 and 6 cm.

In one implementation, the distal tip of the inner catheter is atraumatic and initially is distal to, but abutting, the distal end of the outer catheter. The outer catheter can then be retracted sufficiently to expose the distal opening or openings of the inner catheter. In another implementation, the distal tip of the outer catheter is atraumatic and initially covers the distal end of the inner catheter. The inner catheter can then be advanced sufficiently through the distal end of the outer catheter to expose the distal opening or openings of the inner catheter. The distal end of the outer catheter may be implemented in a variety of ways. These different implementations include a fenestration with at least one partial thickness portion, a thin layer of a material different from the remainder of the catheter, an aperture that is glued closed prior to insertion, or a unidirectional valve.

In another implementation, the outer surface of the outer catheter has ruled markings to guide placement. In another implementation, the length of the catheters is between 6 and 16 cm in length, and between 3 and 12 French in caliber. In another implementation, the catheters may be made of any material compatible with the patient, including latex, silicone, polyurethane, polyethylene, polyvinylchloride, polypropylene, elastomer, Pebax®, polytetrafluoroethylene, or Teflon®. In another implementation, the outer surface of either the inner or outer catheter may be coated with a lubricant. The outer surface of the inner catheter may be coated with an antimicrobial, hydrophilic, or hydrogel material.

In one implementation, the distal end of the catheter system is inserted into a patient's body while the proximal end remains outside. In one implementation, during insertion, the handle allows the catheters to move together, and the catheter system has ruled markings to identify the distance over which the catheter system has been inserted. In one implementation, at the time of insertion, the distal opening or openings of the inner catheter are enclosed by the outer catheter. In one implementation, once the desired length of the catheter system has been inserted, the linear actuator allows, over a limited distance, retraction of the outer catheter, exposing the distal opening or openings of the inner sheath. In another implementation, the linear actuator allows, over a limited distance, sufficient advancement of the inner sheath beyond the distal end of the outer catheter, to expose the distal opening or openings of the inner sheath. In one implementation, the biological sample enters the distal opening or openings and can be collected through the proximal opening of the inner catheter. In one implementation, the catheter system may be removed from the patient after collection of the sample.

In one implementation, the inner catheter is coupled to a stopping mechanism at or about the proximal end, configured to prevent the proximal end of the inner catheter from passing distal to a proximal end of the outer catheter. In one implementation, the outer catheter is coupled to a halting mechanism, configured to limit common motion of the inner and outer catheter. In another implementation, the outer catheter is coupled to a stabilization mechanism configured to conform to a predetermined curved shape.

The present disclosure further relates to a method of collecting a sample of a biological material of a patient. In an implementation, the method includes inserting a catheter system comprising coaxial outer and inner catheters into a lumen of a patient. The coaxial catheters are advanced in a distal direction by means of a proximal handle mechanically engaging the inner catheter and the outer catheter to allow the catheters to have a common motion while a first opening at a distal lateral aspect of the inner catheter is covered by the outer catheter. A linear actuator coupled to at least one of the inner catheter, the outer catheter or the handle is operated to generate a linear motion of one catheter relative to the other catheter, to expose the first opening of the inner catheter. The linear catheter is further configured to limit the relative linear motion to within a predefined range. The biological material is then caused to enter the inner catheter through the first opening of the inner catheter, thereby causing the biological material to flow through the proximal end of the inner catheter to be collected. The catheter system is then removed from the patient.

In one implementation, the linear motion of one catheter is generated by rotating a threaded nut rotatably mounted to the handle, thereby generating linear motion of the outer catheter relative to the inner cathether. In an implementation, the threaded nut is configured to generate linear motion of the inner catheter relative to the outer catheter. In some implementations, the linear motion of one catheter is generated by moving a manual slide mechanism in a distal direction to extend the inner catheter beyond a distal end of the outer catheter. In an implementation, the relative linear movement between the inner catheter and the outer catheter is limited to between 1 and 6 cm.

In one implementation, the relative linear motion of the inner catheter relative to the outer catheter causes the inner catheter to travel through one of a fenestration in a distal end of the outer catheter having a thickness that is less than the thickness of the wall of the remainder of the outer catheter, a thin layer of a material other than a material of that makes the rest of the outer catheter, an aperture that is glued closed prior to insertion or a unidirectional valve.

In some implementations, the lumen of the patient includes a urinary tract of the patient and the patient is less than 4 years of age. In an implementation, the patient is less than 2 years of age.

In one implementation, the catheter system may be used for obtaining a sterile sample of urine from a pediatric patient who is not yet toilet-trained. In another implementation, the catheter system may be used for obtaining a sterile sample of urine from a patient under 2 years of age. In another implementation, the catheter system may be used for obtaining a sterile sample of urine from a patient under 4 years of age.

DESCRIPTION OF FIGURES

FIG. 1 represents a long-axis side view of a catheter system before advancement of inner catheter past the distal tip of the outer catheter. Additionally, FIG. 1 shows an implementation of the catheter system, in which the halting mechanism is a flange system.

FIG. 2 represents a long-axis side view of a catheter system before advancement of inner catheter past the distal tip of the outer catheter. Additionally, FIG. 2 shows an implementation of the catheter system, in which the halting mechanism is a ring.

FIG. 3 depicts a frontal view of the distal end of a catheter system before advancement of inner catheter past the distal tip of the outer catheter. Additionally, FIG. 3 shows an implementation of the catheter system, in which the halting mechanism is a flange system.

FIG. 4 depicts a frontal view of the distal end of a catheter system before advancement of inner catheter past the distal tip of the outer catheter. Additionally, FIG. 4 shows an implementation of the catheter system, in which the halting mechanism is a ring.

FIG. 5 shows a catheter system, which has been deployed within the urethra of a male patient. Additionally.

FIG. 6 shows a catheter system, which has been deployed within the urethra of a female patient. Additionally.

FIG. 7 represents a long-axis side view of a catheter system before advancement of inner catheter past the distal tip of the outer catheter. FIG. 7 shows an implementation of the catheter system, in which the halting mechanism is a flange system. Additionally, FIG. 7 shows a securing mechanism disposed on the outer surface of the outer catheter.

FIG. 8 shows a catheter system, which has been deployed within the urethra of a male patient. FIG. 8 shows an implementation of the catheter system, in which the halting mechanism is a flange system. Additionally, FIG. 8 shows a securing mechanism in an engaged conformation, fastening the outer catheter onto a predetermined curved surface, for example, the head of the penis.

FIG. 9 represents a long-axis side view of a catheter system before advancement of inner catheter past the distal tip of the outer catheter. FIG. 9 shows an implementation of the catheter system, in which relative movement of catheters is facilitated by a narrow protruberance in one catheter and complementary groove in the other catheter. In addition, the distal tip of the outer catheter has a fenestration.

FIG. 10 shows a frontal view of a distal end of a catheter system before advancement of inner catheter past the distal end of the outer catheter. FIG. 10 shows an implementation of the catheter system, in which the halting mechanism is a flange system and the distal tip of the outer catheter has fenestration.

FIG. 11 shows a frontal view of a distal end of a catheter system after the inner catheter has been advanced through a distal tip of the outer catheter. FIG. 11 shows an implementation of the catheter system, in which the halting mechanism is a flange system.

FIGS. 12A-B show an implementation of the catheter system, in which the halting mechanism is a flange system and the distal tip of the outer catheter has a fenestration. Additionally, in the represented implementation the space between the outer catheter and the inner catheter is filled with lubrication gel to ease movement of the inner catheter.

DETAILED DESCRIPTION OF THE INVENTION

The device described herein is a catheter system that includes coaxial inner and outer catheters that may be inserted into a lumen of the body, such as the urinary tract of a subject. The system is designed so that the inner catheter can be advanced relative to the outer catheter or so that the outer catheter can be retracted relative to the inner catheter, by means of a linear actuator, in order to expose openings in the distal end of the inner catheter. The inner catheter is designed so that a biological sample, such as urine, enters the inner catheter through its distal openings. In some cases, the linear actuator may a threaded nut. In other cases, the linear actuator may be a manual slide. Once the sample has been collected, the inner and outer catheters may be removed together.

Currently available urinary catheters are predisposed to collect perimeatal bacteria as they are advanced into the urinary tract, especially in subjects who are difficult to catheterize, such as those who are not toilet trained. The bacteria collected on the distal end of a conventional catheter during insertion can contaminate a urine sample sent for analysis. This contamination may cause a false positive result when the urine is cultured and lead to an incorrect diagnosis of a urinary tract infection. Therefore, there is currently a need in the medical field for a catheter system, in which the collection openings are shielded from contact with perimeatal bacteria during insertion.

The catheter system may be advanced into an existing orifice of a patient, or an orifice that is created before beginning the procedure. The pre-existing orifice may be a urethra, an anus, a vagina, or other orifice that normally exists; the pre-existing orifice may also be an injury or wound, such as a stoma or fistula. The patient may be any animal, including humans as well as non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. The patient may also be livestock such as, cattle, swine, sheep, poultry, and horses, or pets, such as dogs and cats. Furthermore, the patient may be of any species, gender, age, ethnic population, or genotype. Accordingly, the term patient includes males and females, and it includes elderly, elderly-to-adult transition age patients, adults, adult-to-pre-adult transition age patients, and pre-adults, including adolescents, children, toddlers, and infants. The term patient also includes a patient of any body height, body weight, or any organ or body part size or shape. In some implementations, the patient is a human who is around two years old or less, who for example may not be toilet trained.

Figure 1:
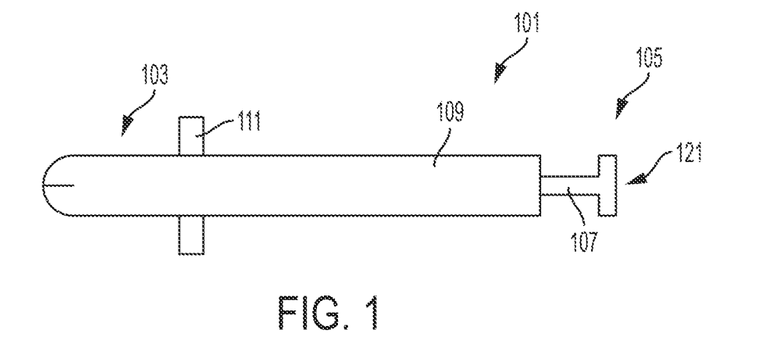
Figure 2:
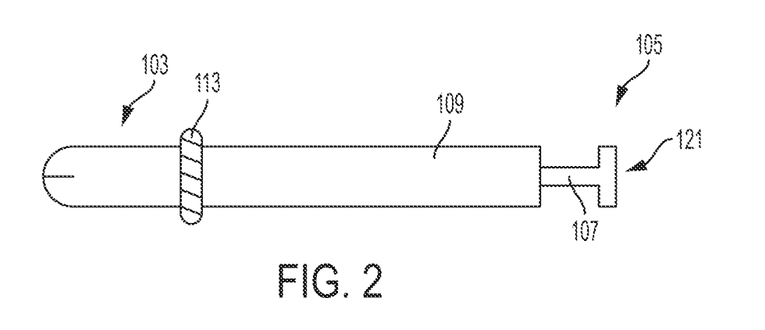

In some implementations, the subject matter disclosed herein relates to a catheter system 101 including coaxial inner 107 and outer 109 catheters, as shown in FIG. 1 and FIG. 2. The catheter system has a distal end 103, which can be advanced into a patient's orifice and a proximal end 105 that remains outside the body, near the operator of the catheter system 101. The outer diameter of the outer catheter 109 is small enough to allow easy introduction into an orifice. The outer diameter of the inner catheter 107 is less than the inner diameter of the outer catheter 109. In some implementations, the outer diameter of the outer catheter 109 is between 5-12 French and that of the inner catheter 107 is between 3-12 French. In another implementation, the outer diameter of the outer catheter 109 can be more than 12 or less than 5 French and the outer diameter of the inner catheter 107 can be more than 12 or less than 3 French. The inner catheter and the outer catheter can be made of any flexible or semi-flexible material including latex, silicone, polyurethane, polyethylene, polyvinylchloride, polypropylene, elastomer, Pebax®, polytetrafluoroethylene, or Teflon®, or any polymer that is biocompatible with a patient's body and will not cause undue discomfort.

Figure 3:
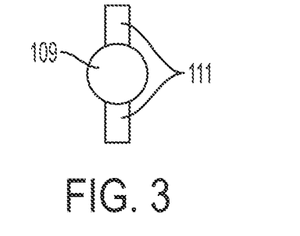

In one implementation of the catheter system 101, the catheter system may further include one or more halting mechanisms disposed on the outer catheter 109, which may limit distal insertion of the outer catheter 109, while still allowing the inner catheter 107 to be advanced distally. In one implementation wherein the patient's orifice is a urethra, this limitation prevents the outer catheter from entering the bladder and introducing any perimeatal bacteria that may have accumulated onto its distal tip during insertion. In one implementation, the halting mechanism may be a flange 111 or a system of flanges as shown in FIG. 1, extending out from the outer surface of the outer catheter 109 at one or multiple locations. FIG. 3 shows a frontal view of the flanges 111 looking down the axis of the catheter system 101. The system of flanges 111 can be two flanges disposed on opposite sides of the outer catheter 109 or it can be a multitude of flanges disposed symmetrically or asymmetrically on the outer catheter 109.

Figure 4:
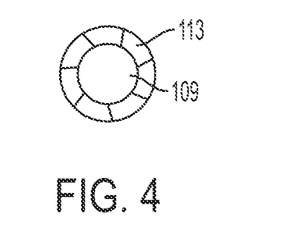

In another implementation, the halting mechanisms is a ring 113 as shown in FIG. 2, extending outward and surrounding the outer surface of the outer catheter 109. FIG. 4 shows a frontal view of the ring 113 looking down the axis of the catheter system 101. The halting mechanism can be made of any flexible, semi-flexible or rigid material including latex, silicone, polyurethane, polyethylene, polyvinylchloride, polypropylene, elastomer, Pebax®, polytetrafluoroethylene, or Teflon®, or any polymer that is biocompatible with a patient's body and will not cause undue discomfort.

The halting mechanism can be placed on the outer catheter 109 by the operator prior to use or can be provided already attached. Furthermore, the halting mechanism can be adjustable along the axis of the outer catheter 109. This can allow, for example, adjustment of the distance from the distal end of the outer catheter 109 to the halting mechanism based on urethral length of the patient to be catheterized. The halting mechanism can also be permanently disposed in at least a portion of the outer catheter 109

In some implementations, the halting mechanism limits distal movement of the outer catheter 109 by coming into contact with the body of the patient, after the catheter system 101 has been advanced through the orifice. Examples of such implementations include but are not limited to the flange and ring implementations of the halting mechanism. This may prevent the outer catheter 109 from advancing any further distally into the orifice, while allowing the inner catheter 107 to be advanced distally further into the orifice.

Figure 5:
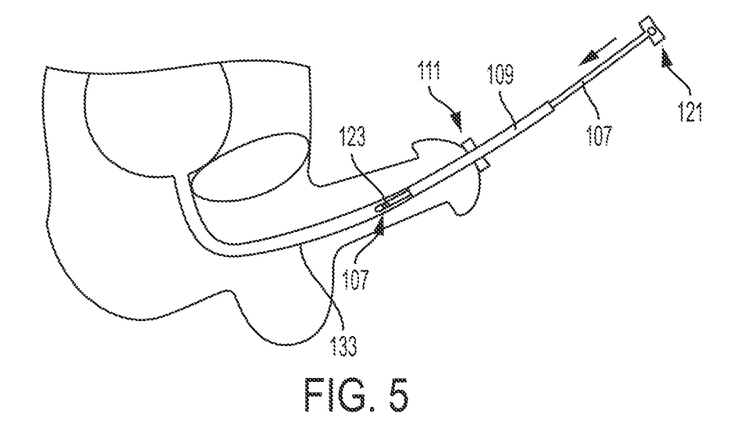
FIG. 5 shows an implementation of the catheter system, in which the halting mechanism is a flange system. Following deployment of a catheter system, the halting mechanism contacts the patient's body in order to limit further distal movement of the outer catheter. This allows for the inner catheter to be advanced distally past the distal tip of the outer catheter.
Figure 6:
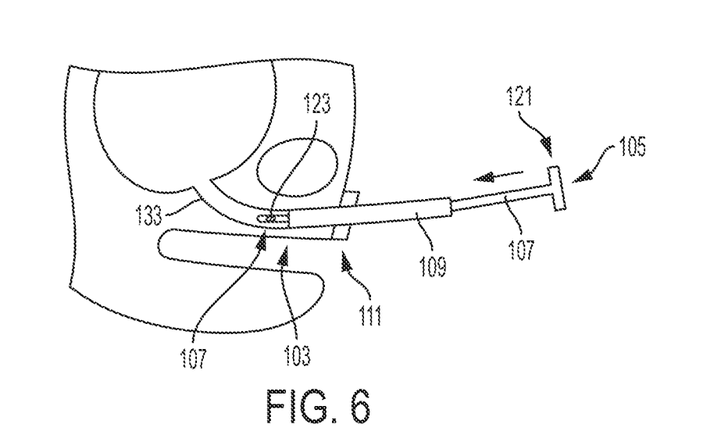
FIG. 6 shows an implementation of the catheter system, in which the halting mechanism is a flange system. Following deployment of a catheter system, the halting mechanism contacts the patient's body in order to limit further distal movement of the outer catheter. This allows for the inner catheter to be advanced distally past the distal tip of the outer catheter.

For example, FIG. 5 illustrates a system of flanges 111 coming into contact with a male patient's body as the catheter system 101 is deployed within the urinary tract of the patient and the inner catheter 107 is advanced further distally into the urethra, past the distal tip of the outer catheter. FIG. 6 illustrates a system of flanges 111 coming into contact with a female patient's body as the catheter system 101 is deployed within the urinary tract of the patient and the inner catheter 107 is advanced further distally into the urethra, past the distal tip of the outer catheter.

In one implementation, the distal end of the inner catheter may ultimately be advanced into the bladder. In another implementation, the distal end of the inner catheter may remain within the urethra.

Figure 7:
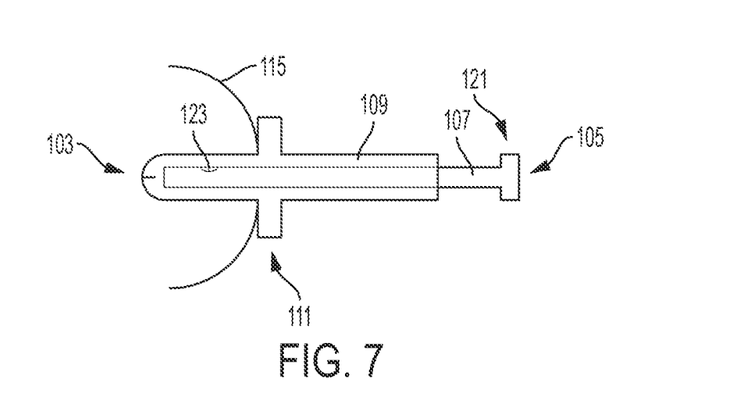
Figure 8:
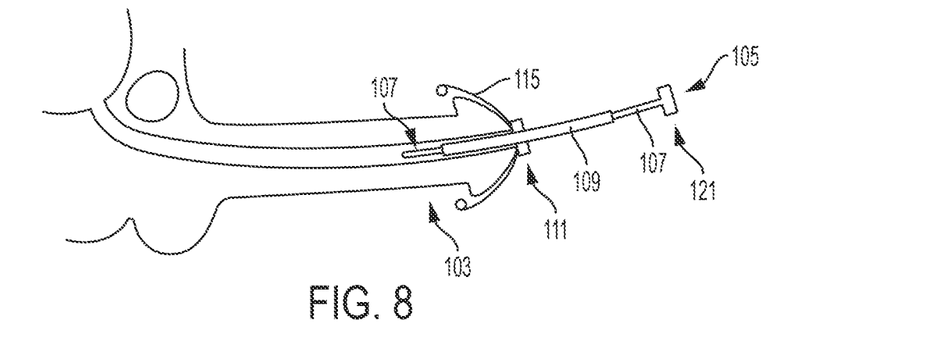

The catheter system 101 may further include a securing mechanism 115 in addition to a halting mechanism for use in male patients' urinary tracts. As shown in FIG. 7, in one implementation the securing mechanism 115 is disposed on the outer surface of the outer catheter 109. When the outer catheter 109 is inserted into a patient, the flanges 111 of the halting mechanism, by coming into contact with the body of the patient, limit the length of the outer catheter 109 that can be inserted, and the securing mechanism 115 further stabilizes the position of the outer catheter by contacting the head of the penis as illustrated in FIG. 8. In another implementation, the securing mechanism 115 may be a collapsible ring or netting that could be advanced forward over the head of the penis while the catheter system 101 is being deployed. The securing mechanism 115 can be permanently attached on the outer catheter or it can be adjustable along the length of the outer catheter. Furthermore, the securing mechanism can be provided separately and attached prior to use of the catheter system or it can be pre-attached to the outer catheter.

The catheter system 101 may further include a stopping mechanism 121 disposed on the inner catheter 107 that prevents entry of the proximal end of the inner catheter 107 into the proximal end of the outer catheter 109 in the proximal-to-distal direction. In one implementation, the stopping mechanism may be a flange 121 or system of flanges disposed on the proximal end of the inner catheter, an example of which is shown in each of FIGS. 1, 2, 5, 6, 7, 8, 9, 12, and 15. When the stopping mechanism is advanced distally to come in contact with or abut the proximal end of the outer catheter 109, it prevents further distal advancement of the inner catheter. In another implementation, such a flange or system of flanges may be located near the proximal end of the inner catheter. The stopping mechanism may also be a ridge, or other protuberance and it may encompass the full circumference of the outer surface of the inner catheter 107, or may be at least one portion of the outer surface of the inner catheter 107. The stopping mechanism may be of the same material as the inner catheter, may be fashioned at the same time as the inner catheter, may be later generated on the inner catheter surface. For example, in an implementation, the stopping mechanism 121 is formed by temporarily melting, i.e., by melting, molding and then resolidifying, the material of the inner catheter to form the desired shape. In another implementation, the stopping mechanism is affixed at a later time. The stopping mechanism may also be of a different material than the inner catheter.

In one implementation of the catheter system described herein, the outer catheter 109 includes a ruled markings indicating to an operator when insertion of the outer catheter 109 should stop. These ruled markings can be based on the length of the urethra (or other lumen accessible through the insertion orifice) of the patient to be catheterized and can be also be customized according to a patient's age or body size (e.g., height and weight). In another implementation, the ruled markings may indicate to an operator when retraction of the outer catheter 109 should stop, once the distal opening or openings 123 of the inner catheter 107 have been exposed 107. In another implementation, the ruled markings may indicate to an operator when advancing the inner catheter 107 should stop, once the distal opening or openings of the inner catheter 107 have been exposed.

Figure 9:
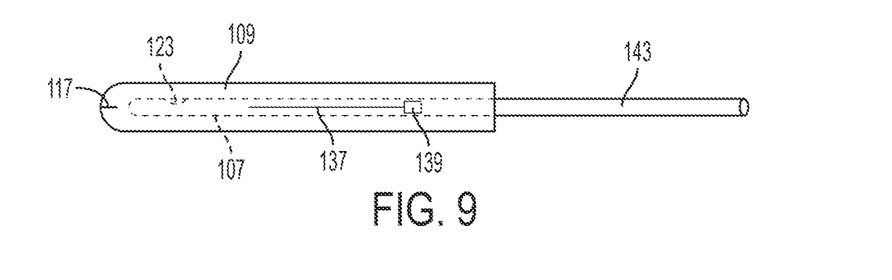

In some implementations of the catheter system 101 that are configured so that the distal portion of the inner catheter 107 is initially just proximal to the distal end of the outer catheter, and then the inner catheter 107 is advanced sufficiently so that the distal opening or openings 123 of the inner catheter 107 are exposed, the distal tip of the outer catheter may be structurally weaker than the rest of the outer catheter 109. In one implementation, the distal tip of the outer catheter is weakened by having one or more portions of the distal tip with decreased thickness of the material, thus, creating a fenestration 117, as illustrated in FIG. 9. Such weakening allows for the inner catheter 107 to be advanced distally past the outer catheter 109 by applying force to break open the distal tip of the outer catheter 109. The necessary force can easily be applied by an operator, for example an adult human, by plunging the inner catheter 107 through the distal tip of the outer catheter 109 in a proximal-to-distal direction.

Figure 10:
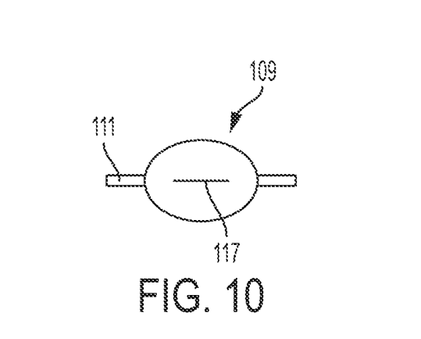
Figure 11:
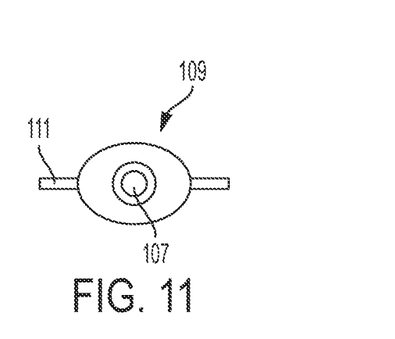

FIG. 10 shows the distal tip of the outer catheter 109 in a frontal view looking down the axis of the outer catheter 109 illustrating the intact fenestration 117 of the distal tip. FIG. 11 shows the disrupted distal tip of the outer catheter 109 in a frontal view looking down the axis of the catheter system 101 with the inner catheter 107 advancing out of the distal tip after the fenestration 117 is broken open. In one implementation, the fenestration may be due to lightly gluing the distal tip closed, holding the distal tip closed by the shape of the distal end of the outer catheter, or sealing the distal tip of the outer catheter 109 with a thin layer of another substance or membrane attached to the outer or inner surface of the outer catheter or any combination of fenestration methods described above. In another implementation, there may be a valve that allows penetration of the inner catheter 107 relative to the outer catheter 109 in the proximal-to-distal axial direction but not in the distal-to-proximal axial direction.

Figure 12A:
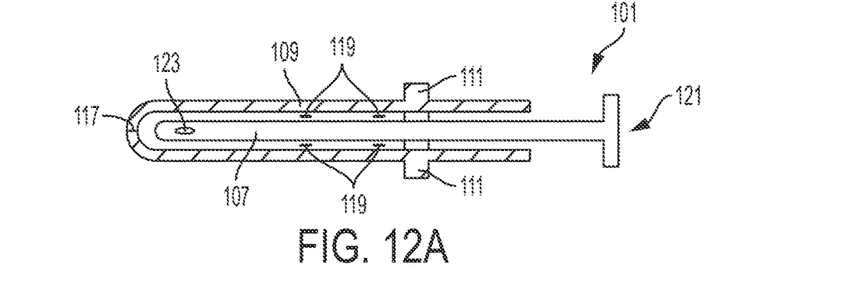
FIG. 12A shows a long-axis cross-sectional view of a catheter system before advancement of the inner catheter past the distal tip of the outer catheter on top.
Figure 12B:
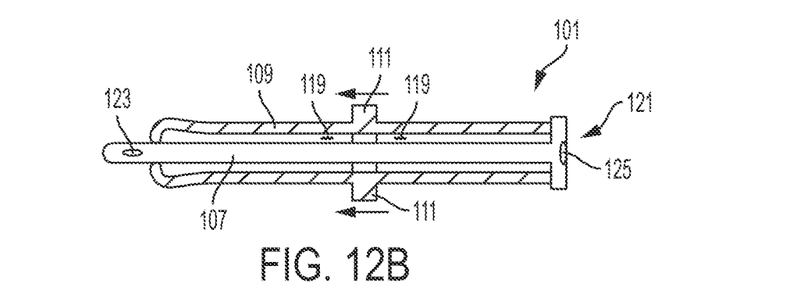
FIG. 12B shows the catheter system following advancement of the inner catheter past the distal tip of the outer catheter.

In one implementation, the catheter system 101 may further include lubrication 119 disposed between the outer surface of the inner catheter 107 and the inner surface of the outer catheter 109 as illustrated in FIGS. 12A-B. This may allow for easier movement of the inner catheter 107 through the outer catheter 109. In another implementation, the catheter system 101 may further include lubrication 119 disposed between the outer surface of the outer catheter 109 and the inner surface of a patient's orifice, such as a urethra 133. See, for example, the illustration of advancement of the catheter system for a male patient, as illustrated in FIG. 5 and for a female patient as illustrated in FIG. 6. This may allow for easier movement of the outer catheter 109 through the patient's orifice. The lubrication 119 may be in the form of a gel or hydrophilic surface, or may be in the form of a layer that can be slid or peeled back. In one implementation, the catheter system 101 may be provided pre-lubricated on the outside or it may be lubricated prior to use.

The outer surface of the outer catheter 109 may be coated or impregnated with an antimicrobial substance, such as silver hydrogel, chlorhexidine-silver, other silver alloy, polyzwitterion/enzyme coatings, gentamicin, minocycline, rifampicin, chlorhexidine-sufadiazine-triclosan, nitrofurazone, other antibiotics or antibiotic liposomes, or antimicrobial peptides AMP.

The catheter system 101 may further include one or more linear actuators to facilitate linear advancement of the inner catheter with respect to the outer catheter, or to facilitate linear retraction of the outer catheter with respect to the inner catheter. In one implementation, the linear actuator limits linear movement of one catheter relative to the other to between 1 and 6 cm.

FIG. 9 illustrates an implementation in which the relative movement between the inner catheter and the outer catheter is facilitated by means of a narrow protruberance 139 disposed on the outer surface of the inner catheter 107 that is fitted through complementary groove 137 in the outer sheath 109 or by means of a narrow protruberance disposed on the inner surface of the outer catheter that is fitted through a complementary groove in the inner sheath. FIG. 9 also shows an atraumatic tip that can comprise the distal end of the outer catheter 141.

In one implementation, force can be applied to the inner catheter 107 by means of a linear actuator configured to advance the inner catheter 107 distally relative to the outer catheter 109, such that the distal end of the inner catheter advances sufficiently beyond the distal tip of the outer catheter 109, to expose the distal opening or openings of the inner catheter 123. The force can be applied to the outer catheter 109 in some implementations by means of a linear actuator configured to retract the outer catheter 109 proximally relative to the inner catheter 107, such that the distal end of the outer catheter is sufficiently proximal to the distal end of the inner catheter to expose the distal opening or openings of the inner catheter 123.

For example, in an implementation, in which the inner catheter 107 is advanced distally relative to the outer catheter 109 in order to expose the distal openings 123 of the inner catheter 107, the distal end of the inner catheter 107 may initially be proximal to the distal end of the outer catheter, and force may be delivered by grasping the portion of the inner catheter 107 itself which has remained outside of the body 143, such as one illustrated in FIG. 9, and advancing it distally.

FIGS. 12A and 12B illustrate another implementation in which the distal end of the inner catheter is initially proximal to the distal end of the outer catheter. In such implementation, force may be delivered to advance the inner catheter through the distal end of the outer catheter, by grasping the manual slide mechanism coupled to the inner catheter, for example, where the manual slide mechanism is the flange of the stopping mechanism 121. As illustrated in FIG. 12B, collection of a desired biological sample, for example urine, from inside a patient ensues, as the sample passes through the opening or openings 123 along the distal shaft of the inner catheter 107, into the inner catheter 107, and exits via the open proximal end 125 of the inner catheter 107, where the sample is then collected by means known in the art, for example in a bottle or bag or any container suitable for collection of a biological sample. In one implementation, the sample is not collected but it is drained from the body.

In one implementation the linear actuator is a screw mechanism. In some implementations of the screw mechanism, at least a portion of the inner surface of the outer catheter 109 and at least a portion of the outer surface of the inner catheter 107 are each threaded, such that rotating one relative to the other causes proximal-to-distal or distal-to-proximal axial movement of one relative to the other.

Figure 13:
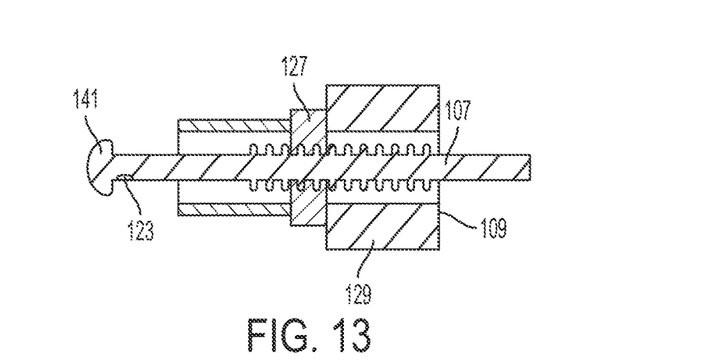
FIG. 13 shows a long-axis cross-sectional view of a catheter system with a threaded nut rotatably mounted to its handle, configured such that the inner catheter passes through the threaded nut and is threaded such that rotation of the threaded nut results in linear motion of the inner catheter relative to the outer catheter.

FIG. 13 illustrates yet another implementation in which the distal end of the inner catheter is initially be proximal to the distal end of the outer catheter. In such implementation, force can be applied to a threaded nut 127 rotatably attached to a handle 129, configured such that the inner catheter 107 passes through the threaded nut and is threaded such that rotation of the threaded nut in one direction results in linear motion of the inner catheter 107 in a distal direction relative to the outer catheter 109 and rotation of the threaded nut 127 in the opposite direction results in linear motion of the inner catheter 107 in a proximal direction relative to the outer catheter 109.

Figure 14:
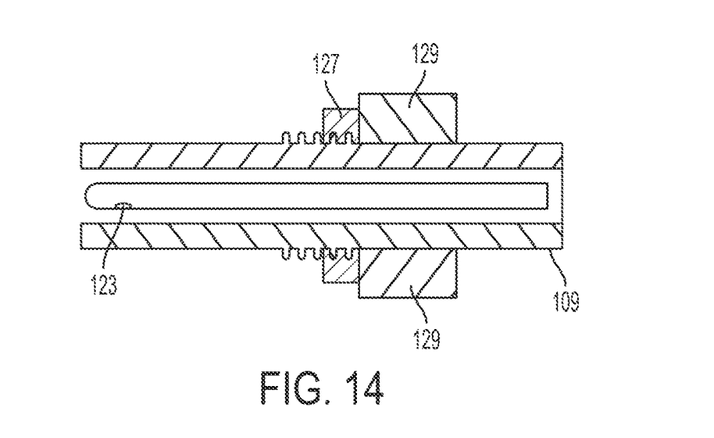
FIG. 14 shows a threaded nut rotatably mounted to a handle, configured such that the outer catheter passes through the threaded nut and is threaded such that rotation of the threaded nut results in linear motion of the outer catheter relative to the inner catheter.

In one implementation of a retracting mechanism, as illustrated in FIG. 14, the threaded nut 127 is configured such that the outer catheter 109 passes through the threaded nut 127 and is threaded such that rotation of the threaded nut 127 in one direction results in linear retraction of the outer catheter 109 relative to the inner catheter 107 and rotation of the threaded nut 127 in the opposite direction results in linear motion of the outer catheter 107 in the distal direction relative to the outer catheter 109. The threaded nut 127 may be of the same material as the catheter, may be fashioned at the same time as the catheter, may be later generated for example by temporarily melting the catheter, or may be affixed at a later time. The threaded nut 127 may also be of a different material compared to the catheter.

Figure 15:
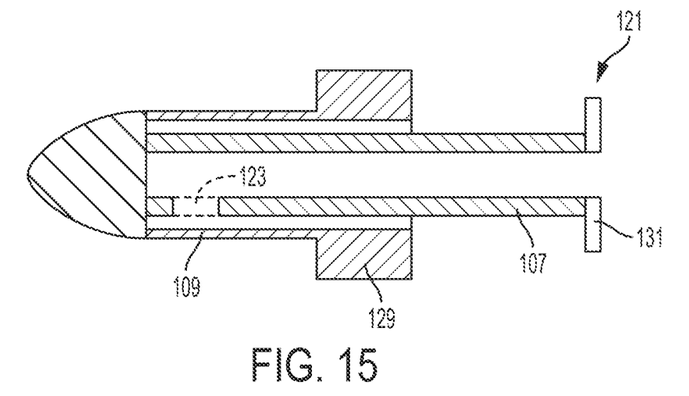
FIG. 15 shows a manual slide mechanism coupled to an inner catheter and handle, configured such that advancement of a slide coupled to the handle causes extension of the inner catheter relative to the outer catheter.

FIG. 15 illustrates an implementation where the linear actuator is a manual slide mechanism 131 coupled to the inner catheter 107 and handle 129. The manual slide mechanism is configured such that distal movement of the manual slide mechanism causes advancement of the inner catheter 107 relative to the outer catheter 109.

In some implementations, as illustrated in FIG. 15, the distal end of the inner catheter may initially be distal to the outer catheter, configured to have an atraumatic tip abutting the outer catheter, and the force to advance the inner catheter may be delivered by means of a manual slide mechanism 121 coupled to the inner catheter 107, as discussed elsewhere herein. In one implementation, the inner catheter 107 is advanced by means of a threaded nut 127 rotatably attached to a handle 129, configured such that the inner catheter 107 passes through the threaded nut, e.g., as shown in FIG. 13, and is threaded such that rotation of the threaded nut results in linear motion of the inner catheter 107 in a distal direction relative to the outer catheter 109, thereby causing the distal opening or openings 123 of the inner catheter 107 to be exposed. FIG. 15 also shows the proximal opening 125 of the inner catheter.

Figure 16:
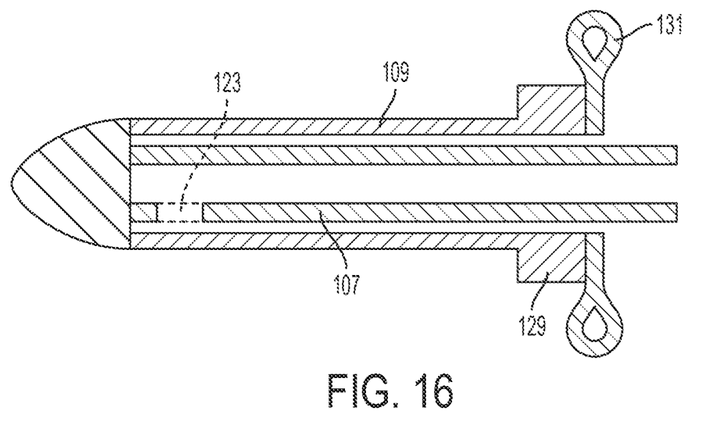
FIG. 16 shows a manual slide mechanism coupled to the outer catheter and handle, configured such that retraction of the manual slide mechanism causes retraction of the outer catheter relative to the inner catheter.

FIG. 16 illustrates an implementation in which the linear actuator is a manual slide mechanism 131 coupled to the outer catheter 109 and handle 129, and the inner catheter 107 is configured to have an atraumatic tip abutting the outer catheter. In such implementation, the manual slide mechanism is configured such that proximal movement of the manual slide mechanism causes retraction of the outer catheter 109 relative to the inner catheter 107.

In some implementations, such as one illustrated in FIG. 16, in which the outer catheter 109 is retracted relative to the inner catheter 107 in order to expose distal openings 123 in the inner catheter 107, force may be delivered by grasping the manual slide mechanism coupled to the outer catheter 131, and retracting the outer catheter in a proximal direction until the distal opening or openings 123 in the inner catheter 107 are exposed. The proximal opening of the inner catheter 125 is also shown. In another implementation, the outer catheter 109 is retracted relative to the inner catheter 107 by rotating a threaded nut 127 rotatably attached to a handle 129, configured such that the outer catheter 109 passes through the threaded nut 127, e.g., as shown in FIG. 14, and is threaded such that rotation of the threaded nut 127 results in linear motion in a proximal direction of the outer catheter 109 relative to the inner catheter 107, thereby causing the distal opening or openings 123 of the inner catheter 107 to be exposed.

The subject matter disclosed herein also relates to a method of use of a catheter system comprising coaxial inner and outer catheters, such that distal opening or openings of the inner catheter are initially surrounded by the outer catheter.

Figure 17:
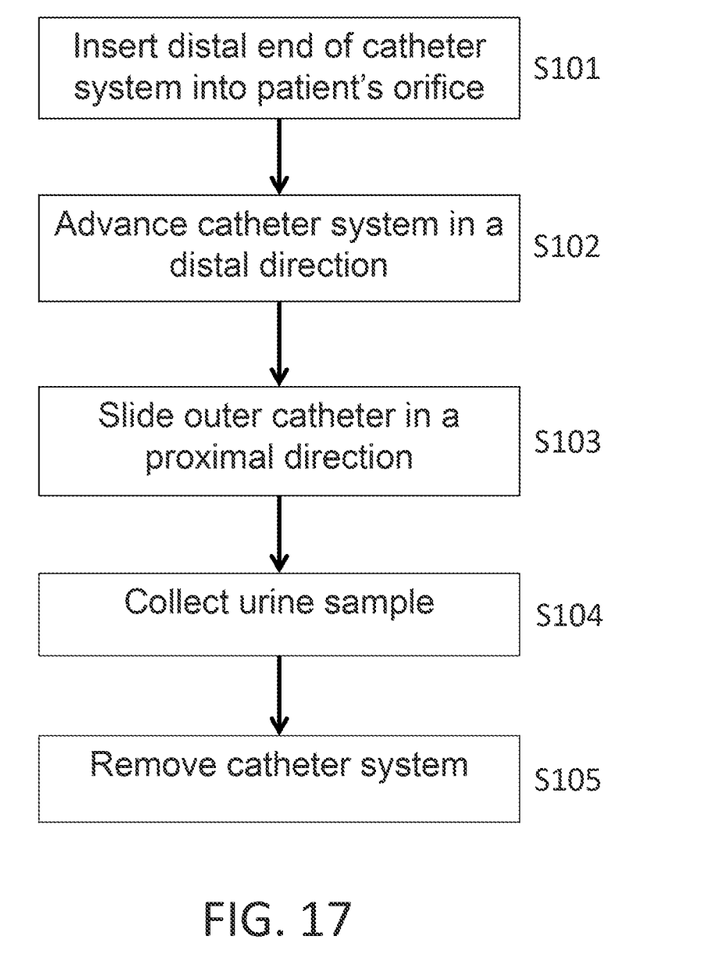
FIG. 17 shows a flow chart for a method of use of the catheter system of the present disclosure in accordance with an implementation.

FIG. 17 shows a flow chart for a method of use of the catheter system of the present disclosure in accordance with an implementation. The method includes, at S101, inserting the distal end of the catheter system into an orifice of a patient in need of catheterization, e.g., the patient's urethra.

At S102, the inner and outer catheters of the catheter system are advanced proximally-to-distally together into the patient's urethra. For example, the catheter system is advanced 1-2 centimeters for female patients at 2 years of age or younger and 4 centimeters for male patients at 2 years of age or younger. In some implementations, at the above lengths, a halting mechanism of the catheter system contacts the body, precluding further insertion. In another implementation, the catheter system may be advanced into the body at a length more or less than 1-2 centimeter for female and more or less than 4 centimeters for male patients.

At S103, once a predetermined length of the outer catheter has been inserted, the distal opening or openings of the inner catheter are exposed by sliding the outer catheter in a proximal direction. For example, the outer catheter is retracted sufficiently distally-to-proximally to expose the distal opening or openings of the inner catheter. Any of the sliding or rotating mechanisms described elsewhere herein may be used for sliding or retracting the outer catheter in the proximal direction.

At S104, a fluid sample is collected. For example, in implementations where the catheter system is inserted into the patient's urethra, a urine sample is collected. By preventing the inner catheter from being exposed to the opening of the urethra, contamination of the urine sample being collected by perimeatal bacteria is avoided, thereby preventing false positives for diseases or illnesses detected based on the urine sample.

At S105, once the required amount of fluid sample is collected, the catheter system is removed from the patient.

Figure 18:
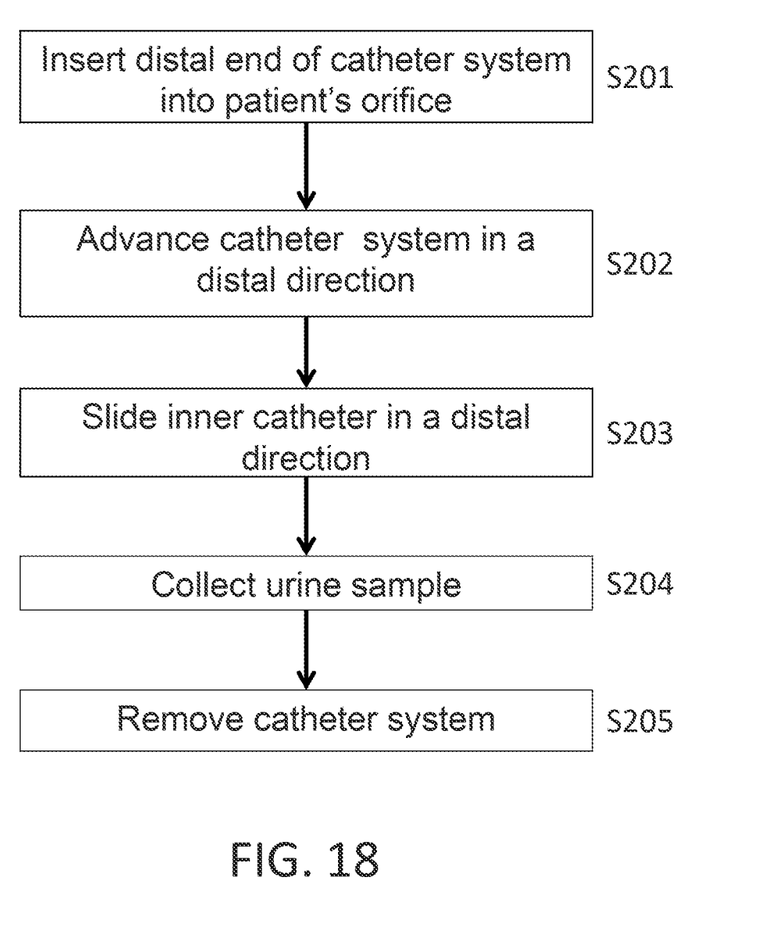
FIG. 18 shows a flow chart for a method of use of the catheter system of the present disclosure in accordance with another implementation.

FIG. 18 shows a flow chart for a method of use of the catheter system of the present disclosure in accordance with another implementation. The method includes, at S201, inserting the distal end of the catheter system into an orifice of a patient in need of catheterization, e.g., the patient's urethra. At S202, the inner and outer catheters of the catheter system are advanced proximally-to-distally together into the patient's urethra.

At S203, once a predetermined length of the outer catheter has been inserted, the distal opening or openings of the inner catheter are exposed by sliding the inner catheter in a distal direction. For example, the inner catheter is advanced sufficiently proximally-to-distally beyond the distal end of the outer catheter to expose the distal opening or openings of the inner catheter. Any of the sliding or rotating mechanisms described elsewhere herein may be used for sliding or retracting the inner catheter in the distal direction.

At S204, a fluid sample, e.g., a urine sample, of the patient is collected.

At S205, once the required amount of fluid sample is collected, the catheter system is removed from the patient.

Using this method, a biological sample that is relatively free of contamination may be obtained from patient. In one implementation, when collection of the biological sample is complete, the catheter system 101 can be withdrawn from the patient by applying force in a distal-to-proximal direction. In some implementations, the operator removes the catheter system 101 from the patient. The operator can be a doctor, nurse, other medical practitioner, medical providers in a clinical or homecare setting, or anyone trained to deploy the catheter system 101. The catheter system 101 may also be deployed by a multiple number of operators, for example, medical practitioners working in a team.

In the above description, reference is made to the accompanying drawings that form a part hereof, and in which is shown by way of illustration specific implementations, which may be practiced. These implementations are described in detail to enable those skilled in the art to practice the invention, and it is to be understood that other implementations may be utilized and that logical changes may be made without departing from the scope of the present invention. The following description of example implementations is, therefore, not to be taken in a limited sense, and the scope of the present invention is defined by the appended claims.

The Abstract is provided to comply with 37 C.F.R. § 1.72b to allow the reader to quickly ascertain the nature and gist of the technical disclosure. The Abstract is submitted with the understanding that it will not be used to interpret or limit the scope or meaning of the claims.

What is claimed is:

1. A pediatric urinary catheter system comprising:
    an inner catheter having a first opening along a distal lateral aspect and a second opening at or about a proximal end;
    an outer catheter coaxial with the inner catheter, wherein a caliber of the outer catheter is between 5 and 12 F;
    a proximal handle to allow the inner catheter and the outer catheter to have a common motion while the first opening of the inner catheter is covered by the outer catheter;

a linear actuator coupled to at least one of the inner catheter, the outer catheter, or the handle configured to, upon actuation, cause linear motion of the inner catheter relative to the outer catheter to expose the first opening of the inner catheter, wherein the linear actuator is further configured to limit the relative linear motion to within a range of between about 1 cm and about 6 cm.

2. The pediatric urinary catheter system of claim 1, wherein the linear actuator comprises a threaded nut rotatably mounted to the handle, configured such that the inner catheter passes through the threaded nut and is threaded such that rotation of the threaded nut results in linear motion of the inner catheter relative to the outer catheter.

3. The pediatric urinary catheter system of claim 1, wherein the linear actuator comprises a threaded nut rotatably mounted to the handle, configured such that the outer catheter passes through the threaded nut and is threaded such that rotation of the threaded nut results in linear motion of the outer catheter relative to the inner catheter.

4. The pediatric urinary catheter system of claim 1, wherein the linear actuator comprises a manual slide mechanism coupled to the outer catheter and handle, configured such that retraction of the manual slide mechanism causes retraction of the outer catheter relative to the inner catheter.

5. The pediatric urinary catheter system of claim 1, wherein the linear actuator comprises a manual slide mechanism coupled to the inner catheter and handle, configured such that extension of a slide coupled to the handle causes extension of the inner catheter relative to the outer catheter.

6. The pediatric urinary catheter system of claim 1, wherein the inner catheter has a distal, atraumatic tip located distal to and abutting a distal end of the outer catheter during insertion of the catheter system.

7. The pediatric urinary catheter system of claim 1, wherein the outer catheter has a distal, atraumatic tip located distal to a distal end of the inner catheter during insertion of the catheter system.

8. The pediatric urinary catheter system of claim 1, wherein the outer catheter has ruled markings along an outer surface.

9. The pediatric urinary catheter system of claim 1, wherein the length of the each of the coaxial catheters is between 6 and 16 cm.

10. The pediatric urinary catheter system of claim 1, wherein a caliber of the inner catheter is between 3 and 12 F.

11. The pediatric urinary catheter system of claim 1, wherein the catheter material is latex, silicone, polyurethane, polyethylene, polyvinylchloride, polypropylene, elastomer, polyether block amide, or polytetrafluoroethylene.

12. The pediatric urinary catheter system of claim 1, wherein an outer surface of the inner catheter or the outer catheter is coated with a lubricant.

13. The pediatric urinary catheter system of claim 1, wherein an outer surface of the catheters is coated with an antibacterial, hydrophilic, or hydrogel material.

14. The pediatric urinary catheter system of claim 1, wherein a distal end of the outer catheter comprises one or more of the following:
a fenestration with at least one partial thickness portion;
a thin layer of a material other than a material that makes up the outer catheter;
an aperture that is glued closed prior to insertion; or
a unidirectional valve.

15. A method for sampling urine of a patient, comprising:
inserting a urinary catheter system, further comprising coaxial outer and inner catheters, into a lumen of a human patient of no more than 2 years of age, wherein a caliber of the outer catheter of the urinary catheter system is between 5 and 12 F;
advancing the coaxial catheters in a distal direction by means of a proximal handle mechanically engaging the inner catheter and the outer catheter, to allow the catheters to a have common motion, while a first opening at a distal lateral aspect of the inner catheter is covered by the outer catheter;
operating a linear actuator, coupled to at least one of the inner catheter, the outer catheter or the handle, to generate linear motion of one catheter relative to the other catheter, to expose the first opening of the inner catheter, wherein the linear actuator is further configured to limit the relative linear motion to a range of between about 1 cm and about 6 cm;
causing urine of the patient to enter the inner catheter through the first opening of the inner catheter; and
removing the catheter system from the patient.

16. The method of claim 15, wherein generating linear motion of one catheter comprises rotating a threaded nut rotatably mounted to the handle, thereby generating linear motion of the outer catheter relative to the inner catheter.

17. The method of claim 15, wherein generating linear motion of one catheter comprises rotating a threaded nut rotatably mounted to the handle, thereby generating linear motion of the inner catheter relative to the outer catheter.

18. The method of claim 15, wherein generating linear motion of one catheter comprises moving in a proximal direction a manual slide mechanism to retract the outer catheter relative to the inner catheter.

19. The method of claim 15, wherein generating linear motion of one catheter comprises moving a manual slide mechanism in a distal direction to extend the inner catheter beyond a distal end of the outer catheter.

20. The method of claim 15, wherein the generation of relative linear motion of the inner catheter relative to the outer catheter causes the inner catheter to travel through one of:
a fenestration in a distal end of the outer catheter having a thickness that is less than the thickness of the wall of the remainder of the outer catheter;
a thin layer of a material other than a material that makes up the outer catheter;
an aperture that is glued closed prior to insertion; or
a unidirectional valve.

21. The pediatric urinary catheter system of claim 1, wherein the inner catheter is coupled to a stopping mechanism at or about the proximal end, configured to prevent the proximal end of the inner catheter from passing distal to a proximal end of the outer catheter.

22. The pediatric urinary catheter system of claim 1, wherein the outer catheter is coupled to a halting mechanism, configured to limit common motion of the inner and outer catheter.

23. The pediatric urinary catheter system of claim 1, wherein the outer catheter is coupled to a stabilization mechanism configured to conform to a predetermined curved shape.

24. The pediatric urinary catheter system of claim 1, wherein the proximal handle, that allows the inner catheter and the outer catheter to have a common motion, mechanically engages the inner catheter and the outer catheter.

* * * * *